United States Patent
Kitano

(10) Patent No.: US 7,968,521 B2
(45) Date of Patent: Jun. 28, 2011

(54) STABLE CYSTAL OF PROTECTED PSEUDOURIDINE

(75) Inventor: Kenji Kitano, Ibaraki (JP)

(73) Assignee: Yamasa Corporation, Chiba (JP)

( * ) Notice: Subject to any disclaimer, the term of this patent is extended or adjusted under 35 U.S.C. 154(b) by 766 days.

(21) Appl. No.: 11/993,011

(22) PCT Filed: Jun. 21, 2006

(86) PCT No.: PCT/JP2006/312426
§ 371 (c)(1),
(2), (4) Date: Dec. 18, 2007

(87) PCT Pub. No.: WO2006/137447
PCT Pub. Date: Dec. 28, 2006

(65) Prior Publication Data
US 2010/0216985 A1    Aug. 26, 2010

(30) Foreign Application Priority Data

Jun. 24, 2005  (JP) .................................. 2005-184188
Nov. 9, 2005   (JP) .................................. 2005-324239

(51) Int. Cl.
*A01N 43/04*   (2006.01)
*A61K 31/70*   (2006.01)
*C07H 1/00*    (2006.01)
*C07H 5/04*    (2006.01)

(52) U.S. Cl. ......... 514/23; 536/18.7; 536/29.2; 536/124

(58) Field of Classification Search ........................ None
See application file for complete search history.

(56) References Cited

FOREIGN PATENT DOCUMENTS

| JP | 2-091022 | 3/1990 |
| JP | 2-104586 | 4/1990 |
| JP | 2-196787 | 8/1990 |
| WO | 96/018736 | 6/1996 |

OTHER PUBLICATIONS

Pfister et al., Nucleosides, Part LIX, Helvetica Chimica Acta, 1995, vol. 78, No. 7, pp. 1705-1737.*

Pfister, Magdalena et al., Nucleosides. Part LIX. The 2-(4-nitrophenyl) ethylsulfonyl (npes) group: A new type of protection in nucleoside chemistry, Helvetica Chimica Acta, 1995, vol. 78, No. 7, pp. 1705 to 1737, particularly, pp. 1709, 1723.

Agris, P.F. et al., Site-selected introduction of modified purine and pyrimidine ribonucleosides into RNA by automated phosphoramidite chemistry, Biochimie, 1995, vol. 77, No. 1/2, pp. 125 to 134, particularly, p. 128.

Yang, Zaiwan et al., Nucleic acid chemistry. V. Synthesis of modified ribonucleotides and oligonucleotides, Huaxue Xuebao, 1986, vol. 44, No. 11, pp. 1106-1112 (abstract) CAplus (online), AN 1987:637207, DN 107:237207.

European Search Report issued on Apr. 3, 2009, for corresponding Patent Application EP 06767085.1.

* cited by examiner

*Primary Examiner* — Traviss C McIntosh, III
(74) *Attorney, Agent, or Firm* — K&L Gates LLP

(57) ABSTRACT

A stable and high-purity protected pseudouridine in crystal form is provided represented by the following structural formula:

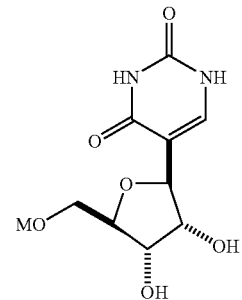

wherein M represents a trityl group or a derivative thereof, which is a useful material for producing an RNA oligomer or a similar substance. A method for producing the crystalline protected pseudouridine is also provided, which method includes crystallizing a protected pseudouridine from a solution containing the protected pseudouridine, by use of an ester solvent and/or an alcoholic solvent. The method, which does not need a silica gel column treatment, can be performed in a simple manner, does not impose a load on the environment, and realizes low-cost production of a target crystalline protected pseudouridine.

8 Claims, 4 Drawing Sheets

STABLE CYSTAL OF PROTECTED PSEUDOURIDINE

CROSS REFERENCE TO RELATED APPLICATIONS

The present application claims priority to Japanese Patent Document No. 2005-184188 filed on Jun. 24, 2005, and Japanese Patent Document No. 2005-324239 filed on Nov. 9, 2005, the disclosures of which are herein incorporated by reference.

BACKGROUND

The present invention relates to a protected pseudouridine in crystal form (hereinafter referred to as a crystalline protected pseudouridine), which is a useful material for producing an RNA oligomer or a similar substance, and to a method for producing the crystalline protected pseudouridine.

A phosphoroamidite derivative of pseudouridine is employed as a material for the chemical autosynthesis of RNA oligomers including a modified nucleoside. For example, a phosphoroamidite derivative of pseudouridine is used as a starting material in the synthesis of tRNA of yeast (see Biochimie, 77, 125 (1995)).

In recent years, genome-base drug discovery, which employs aptamers, RNA interference, etc., has become of interest, and a phosphoroamidite derivative of pseudouridine is employed as one of the starting materials for synthesizing such oligomers.

The chemical autosyntesis of an RNA oligomer including pseudouridine is usually carried out by employment of a 3'-phosphoroamidite derivative of pseudouridine whose 5'- and 2'-hydroxyl groups are protected with an appropriate protective group. Specifically, the aforementioned document discloses a 3'-(2-cyanoethyl-N,N-diisopropyl)phosphoroamidite derivative of pseudouridine, whose 5'-position is protected with a 4,4'-dimethoxytrityl (DMTr) group and whose 2'-position is protected with a t-butyldimethylsilyl (TBDMS) group.

Such a phosphoroamidite derivative is synthesized through, sequentially, introducing DMTr into the 5'-position of pseudouridine, introducing TBDMS into the 2'-position, and introducing an amidite into the 3'-position. In the first step of introducing DMTr into pseudouridine, 4,4'-dimethoxytrityl chloride (DMTrCl) is reacted with pseudouridine in pyridine at room temperature, followed by phase separation and purification by means of a silica gel column, to thereby recover a protected species of interest. The aforementioned document does not disclose properties of the 5'-DMTr derivative of pseudouridine. However, another document (Helvetica Chimica Acta, 78, 1705 (1995)) discloses that the 5'-DMTr derivative of pseudouridine synthesized in the same procedure assumes the form of colorless foam.

Non-Patent Document 1: Biochimie, 77, 125 (1995)
Non-Patent Document 2: HELVETICA CHIMICA ACTA, 78, 1705 (1995)

SUMMARY

In the aforementioned DMTr introducing reaction, protected pseudouridine species in which DMTr has been introduced not only into the 5'-position of pseudouridine but also into 2'-position and/or the 3'-position are by-produced. These by-products cause side reactions in the second step of introducing TBDMS into the 2'-position, thereby lowering the yield of a protected pseudouridine of interest, which is a problem. Therefore, after DMTr introducing reaction, a purification step by means of a silica gel column is considered essential in the art.

However, since purification by use of a silica gel column is intricate and requires a large amount of organic solvent, the process adversely affects the environment and is a main cause of increasing production cost of the target compound.

The foam-like 5-O-(4,4'-dimethoxytrityl)pseudouridine produced through the aforementioned conventional technique is an amorphous product. Thus, this product has problems including poor stability and variation in quality.

The present inventor has carried out extensive studies in order to solve the aforementioned problems, and has quite surprisingly found that crystals of 5'-O-(4,4'-dimethoxytrityl) pseudouridine can be recovered through crystallization by use of an organic ester solvent and/or an organic alcoholic solvent without performance of a purification step by means of a silica gel column, and the recovered crystals are high-purity and stable. The present invention has been accomplished on the basis of further development of these findings.

Accordingly, the present invention provides a crystalline protected pseudouridine represented by the following structural formula:

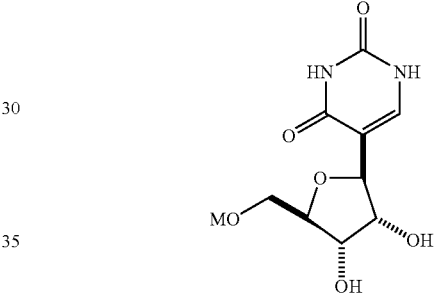

(wherein M represents a trityl group or a derivative thereof).

In one embodiment of the present invention, M in the above structural formula may be a dimethoxytrityl group, a monomethoxytrityl group, or a trityl group. For example, M may be a 4,4'-dimethoxytrityl group.

The present invention also provides a method for producing a crystalline protected pseudouridine represented by the aforementioned structural formula, characterized in that the method comprises crystallizing a protected pseudouridine from a solution containing the protected pseudouridine, by use of an ester solvent and/or an alcoholic solvent.

In one preferred embodiment of the method according to the present invention, the ester solvent may be an acetic acid ester such as ethyl acetate, methyl acetate, or n-butyl acetate, and the alcoholic solvent may be a linear or branched alcohol having seven or less carbons such as ethanol, methanol, or isopropanol. Alternatively, in the present invention, crude target crystals produced from an ester solvent may be recrystallized from an alcoholic solvent.

Additional features and advantages of the present invention are described in, and will be apparent from, the following Detailed Description and the Figures.

DETAILED DESCRIPTION

The Crystalline Product of the Present Invention

The crystalline product of the present invention is directed to a crystalline protected pseudouridine represented by the following structural formula:

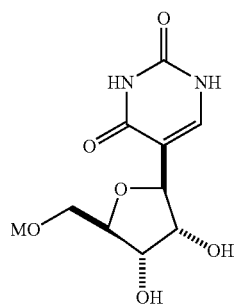

(wherein M represents a trityl group or a derivative thereof).

Examples of the derivative of the trityl group denoted by M in the above formula include a dimethoxytrityl group and a monomethoxytrityl group. Of these, a 4,4'-dimethoxytrityl group is a particularly preferred protective group.

These crystalline protected pseudouridines have a target crystalline protected pseudouridine content, as determined through HPLC analysis, of 95% (w/w) or more, preferably 98% or more, even when no purification step by means of a silica gel column is performed. The analogous compound content is 5% or less, preferably 2% or less.

The analogous compound refers to a ditrityl derivative of pseudouridine such as 2',5'-O-di(trityl or a derivative thereof) pseudouridine or 3',5'-O-di(trityl or a derivative thereof) pseudouridine.

The crystalline protected pseudouridine of the present invention exhibits characteristic peaks in powder X-ray analysis. When analyzed by means of a powder X-ray diffractometer using a Cu—Kα ray, crystalline 5'-O-(4,4'-dimethoxytrityl)pseudouridine exhibits, as shown in the Examples hereinbelow, characteristic peaks near the diffraction angles (2θ) of 4.6, 8.0, 9.3, 12.3, 12.9, 14.5, 16.6, 17.3, 18.6, 19.1, 20.3, 21.4, 21.8, 23.7, 24.7, and 26.1(°) (see FIG. 1).

Figure 3:
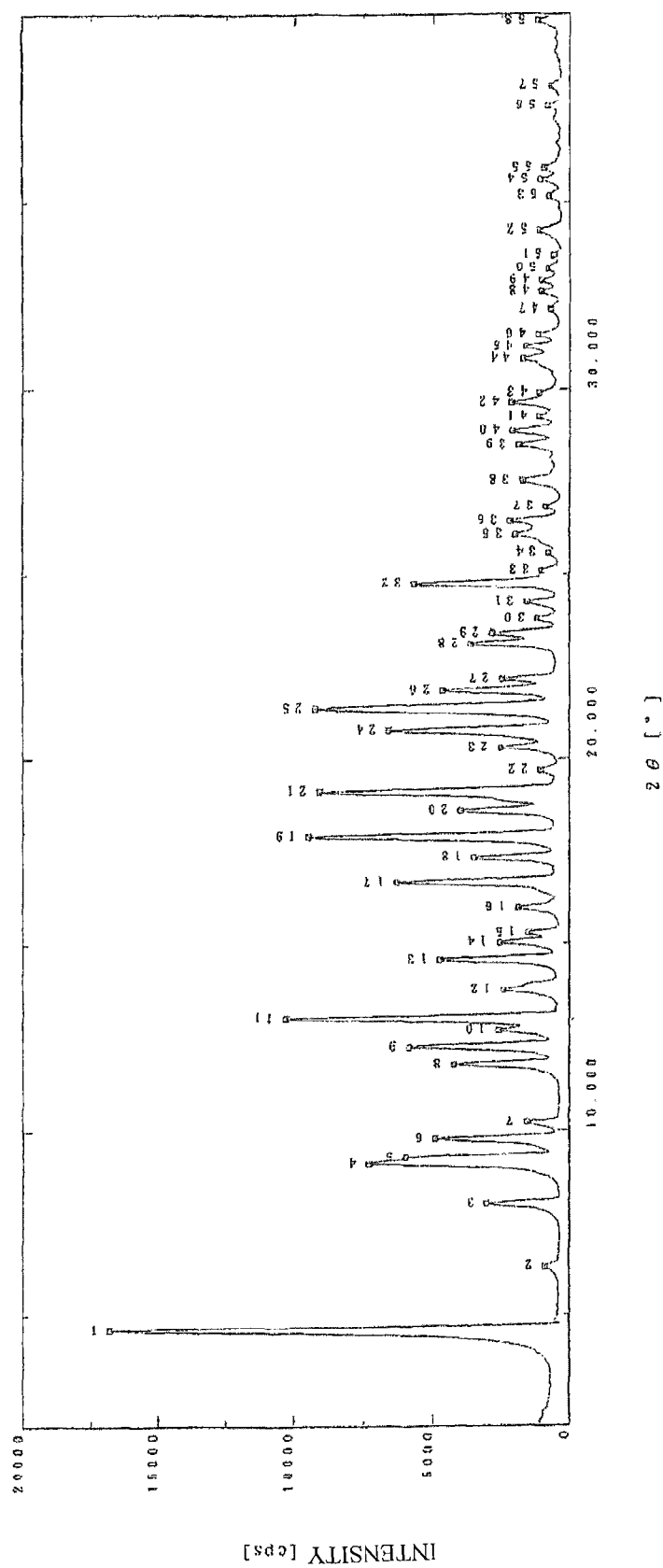
FIG. 3 is a powder X-ray diffraction pattern of crystalline 5'-O-tritylpseudouridine.
Figure 4:
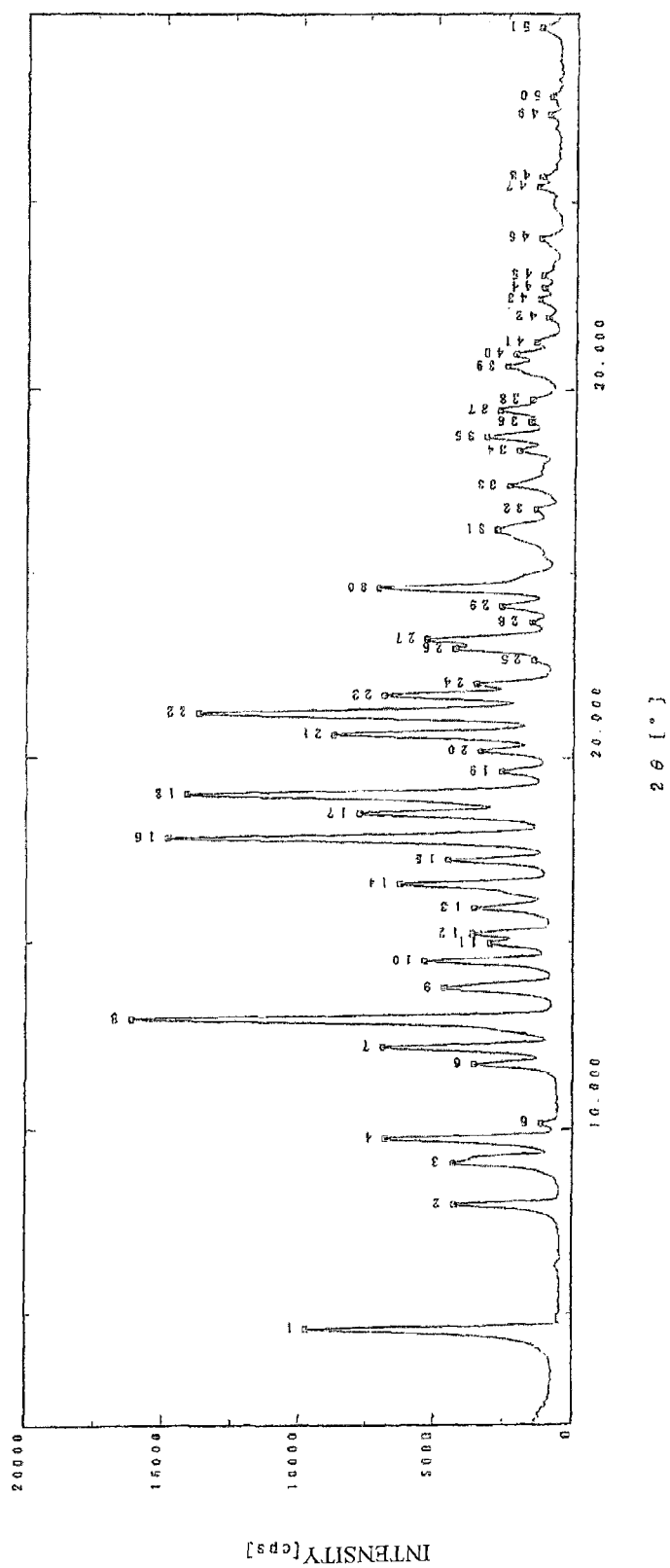
FIG. 4 is a powder X-ray diffraction pattern of crystalline 5'-O-(4-methoxytrityl)pseudouridine.

Crystalline 5'-O-tritylpseudouridine exhibits characteristic peaks at the diffraction angles (2θ) of 4.60, 9.10, 13.02, 14.58, 16.68, 17.92, 19.14, 20.78, 21.36, and 24.76 (see FIG. 3), whereas crystalline 5'-O-(4-monomethoxytrityl)pseudouridine exhibits characteristic peaks at the diffraction angles (2θ) of 4.60, 9.76, 12.20, 12.94, 16.60, 17.84, 18.52, 19.04, 20.66, 21.24, 21.70, and 24.60 (see FIG. 4).

In general, the diffraction angles (2θ) in powder X-ray diffractometry may include an error less than 5%. Therefore, the crystalline protected pseudouridine of the present invention encompasses both a crystalline product which exhibits diffraction peaks in powder X-ray diffractometry at diffraction angles completely coinciding with those attributed to the corresponding crystalline product, and a crystalline product which exhibits diffraction peaks at diffraction angles coinciding, within an error less than 5%, with those attributed to the corresponding crystalline product.

[Method of Producing the Crystalline Product of the Present Invention]

The crystalline product of the present invention may be prepared through crystallization of a protected pseudouridine from a solution containing the protected pseudouridine, by use of an ester solvent and/or an alcoholic solvent.

The ester solvent may be an acetic acid ester such as ethyl acetate, methyl acetate, or n-butyl acetate, and the alcoholic solvent may be an linear or branched alcohol having seven or less carbons such as ethanol, methanol, or isopropanol. Among these solvents, ethyl acetate and ethanol are particularly preferred.

No particular limitation is imposed on the method of crystallizing a protected pseudouridine. In order to recover high-purity crystals, preferably, crude crystals of the protected pseudouridine are recovered from an ester solvent, and the crude crystals are recrystallized from an alcoholic solvent.

In a specific procedure, firstly, pseudouridine is reacted with a chloride of a protective group at room temperature in an organic solvent for several hours. After reaction, the reaction mixture is phase-separated by use of water and an ester solvent. The organic layer is concentrated under reduced pressure, and the residue is co-boiled with an ester solvent, whereby a protected pseudouridine is dissolved in the ester solvent by heating.

After dissolution by heating, a liquid containing the protected pseudouridine is allowed to stand at room temperature (23 to 27° C.), to thereby recover crude crystals of the protected pseudouridine. After co-boiling with an alcoholic solvent, the crude crystals are dissolved in an alcoholic solvent with heating, and the solution is allowed to stand at room temperature. The precipitated crystals are recovered through filtration, to thereby recover high-purity crystals of the protected pseudouridine. In the case where percent crystal recovery is low, the filtrate after crystallization may be further subjected to the aforementioned crystallization process, to thereby recover second crystals.

The thus-produced crystals are dried at room temperature to 100° C., preferably 60 to 90° C., for 3 to 6 hours under reduced pressure, to thereby yield a final product.

EXAMPLES

The present invention will next be described in detail by way of the Examples and Test Examples, which should not be construed as limiting the invention thereto.

Example 1

Production of Crystalline 5'-O-(4,4'-dimethoxytrityl) pseudouridine

Pseudouridine (4.77 g, 18.3 mmol) was dehydrated through co-boiling twice with pyridine (36 mL) which had been dried with Molecular Sieves 4 A and suspended in pyridine (72 mL). Under stirring at room temperature, 4,4'-dimethoxytrityl chloride (7.45 g, 22 mmol) was added to the suspension. The mixture was placed in a vessel closed with a ground glass stopper and stirred at room temperature for two hours.

Water (7 mL) was added to the reaction mixture at room temperature, and the mixture was concentrated under reduced pressure. Ethyl acetate (110 mL) was added to the residue, and the mixture was washed twice with water (30 mL) and once with aqueous saturated sodium bicarbonate (30 mL). The organic layer was dried over sodium sulfate anhydrate, followed by concentration under reduced pressure. The residue was co-boiled thrice with ethyl acetate (55 mL). The residue was dissolved in ethyl acetate (55 mL) with heating. The solution was allowed to stand at 25° C. for 22 hours, and the precipitated crystals were recovered through filtration by means of a glass filter.

The crystals recovered through filtration were washed once with ethyl acetate, and suspended in ethyl acetate (93 mL) with heating. The suspension was allowed to stand at 25° C. for one hour, and the precipitated crystals were recovered through filtration by means of a glass filter. The crystals recovered through filtration were washed once with ethyl acetate, and co-boiled thrice with ethanol (74 mL). The residue was dissolved in ethanol (74 mL) with heating, and the solution was allowed to stand at 25° C. for 21 hours. The precipitated crystals were recovered through filtration by means of a Kiriyama funnel (product of Kiriyama Glass Co.).

The crystals were washed once with ethyl acetate and dried under reduced pressure (5 mmHg) at 90° C. for three hours, to thereby yield 4.21 g of white needles (first crystals) (42%). The filtrate from which the first crystals had been separated was concentrated under reduced pressure, and the residue was co-boiled once with ethanol (18 mL). The residue was dissolved in ethanol (18 mL) with heating. A portion (3 mg) of the first crystals was added as seed crystals to the solution, and the solution was allowed to stand at 25° C. for three days. Similar to recovery of the first crystals, the crystals were also recovered through filtration, followed by drying, to thereby yield 1.62 g of white needles (second crystals) (16%).

Figure 1:
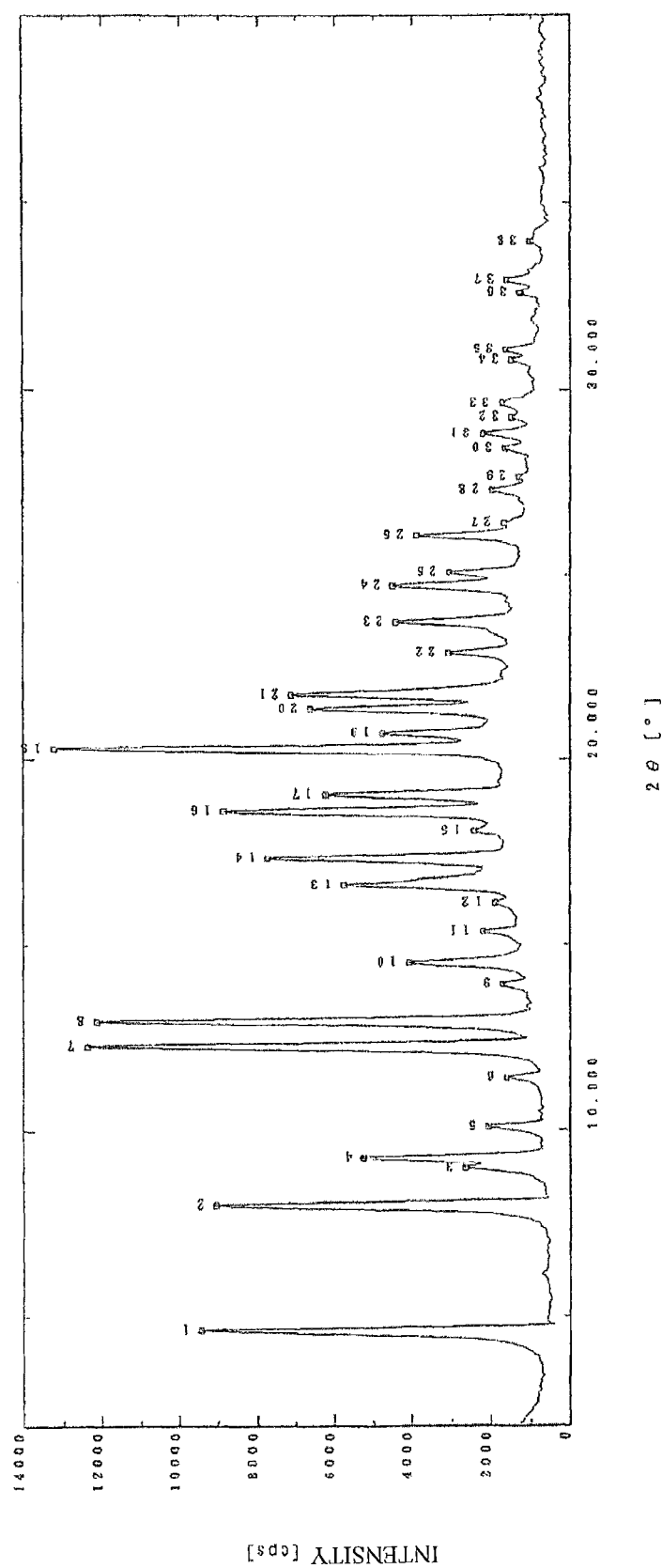
FIG. 1 is a powder X-ray diffraction pattern of crystalline 5'-O-(4,4'-dimethoxytrityl)pseudouridine.

Through powder X-ray diffractometry, the thus-yielded crystals (first crystals) exhibited characteristic peaks at the diffraction angles (2θ) of 4.62, 8.00, 9.26, 12.26, 12.92, 14.52, 16.62, 17.34, 18.62, 19.06, 20.32, 21.38, 21.76, 23.72, 24.72, and 26.06 (see FIG. 1).

Figure 2:
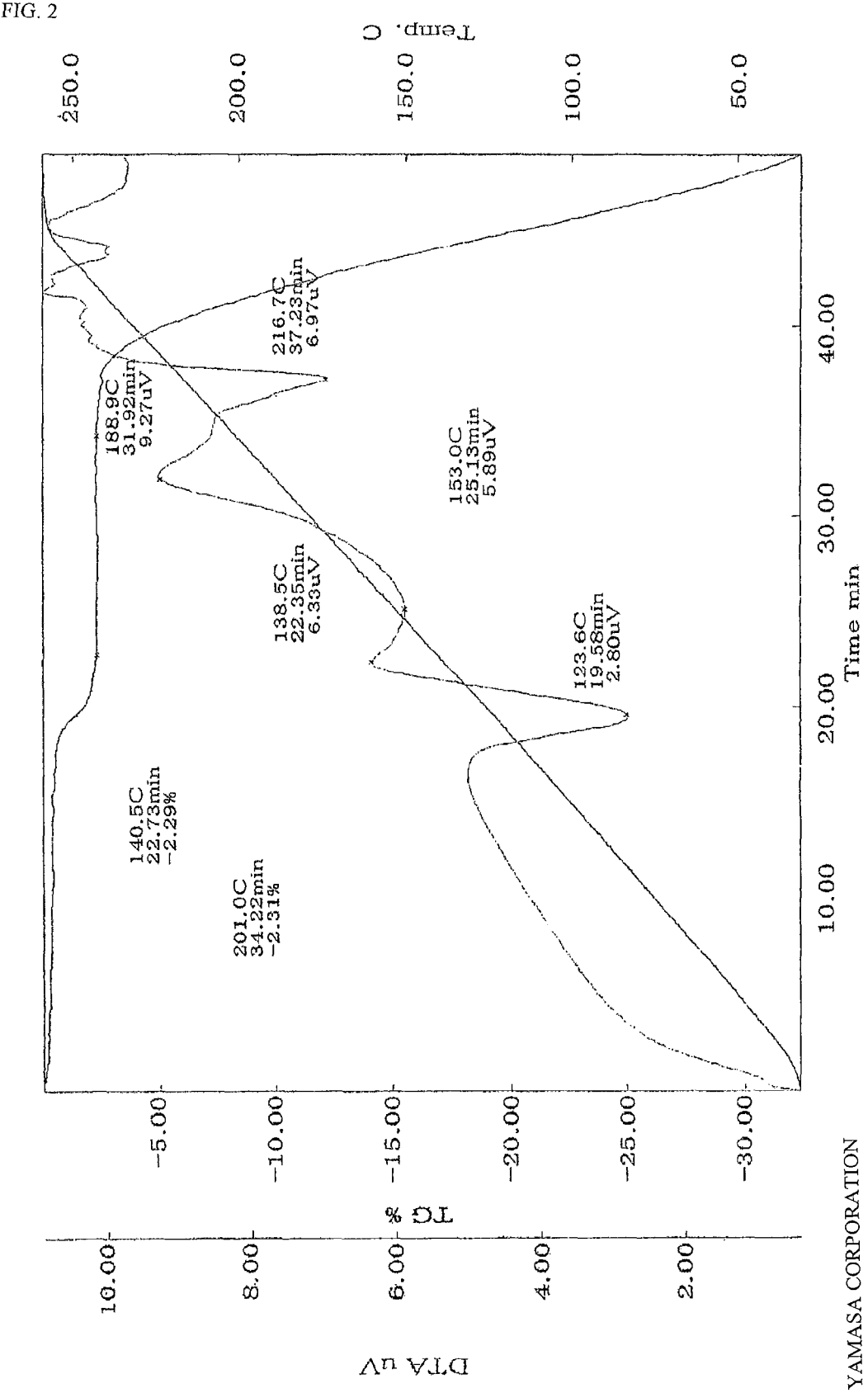
FIG. 2 is a chart showing TG/DTA curves of crystalline 5'-O-(4,4'-dimethoxytrityl)pseudouridine.

Through analysis by means of a thermogravimetric/differential thermal (TG/DTA) analyzer (temperature elevation rate: 5° C./min), a characteristic endothermal peak was observed at about 123.6° C. (see FIG. 2).

NMR analysis results are as follows. Note that the analytical results of the second crystals obtained by means of the above apparatuses are equivalent to those of the first crystals. 1H-NMR: (DMSO-d6) 10.9-11.2 (br d, 2H, NH), 7.18-7.42 (m, 10H, Ar—H and H-6), 6.88 (d, J=8.8 Hz, 4H, Ar—H), 4.99 (br s, 1H, OH), 4.76 (d, J=5.7 Hz, 1H, OH), 4.53 (d, J=3.8 Hz, 1H, H-1'), 3.81-3.95 (m, 3H, H-2', 3' and 4'), 3.74 (s, 6H, OMe), 3.12 (d, J=1.5, 10.2 Hz, 1H, H-5'), 3.07 (d, J=5.1, 11.2 Hz, 1H, H-5').

Example 2

Production of Crystalline 5'-O-tritylpseudouridine

Pseudouridine (0.61 g, 2.5 mmol) was dehydrated through co-boiling twice with pyridine (5 mL) which had been dried with Molecular Sieves 4 A and suspended in pyridine (9.8 mL). Under stirring at room temperature, trityl chloride (0.836 g, 3 mmol) was added to the suspension. The mixture was placed in a vessel closed with a ground glass stopper and stirred at room temperature for one day.

Water (1 mL) was added to the reaction mixture at room temperature, and the mixture was concentrated under reduced pressure. Ethyl acetate (15 mL) was added to the residue, and the mixture was washed twice with water (4 mL) and once with aqueous saturated sodium bicarbonate (4 mL). The organic layer was dried over sodium sulfate anhydrate, followed by concentration under reduced pressure. The residue was co-boiled twice with ethyl acetate (7.7 mL). The residue was dissolved in ethanol (24 mL) with heating. The solution was allowed to stand at 25° C. for two days, and the precipitated crystals were recovered through filtration by means of a funnel (product of Kiriyama Glass Co.).

The crystals were washed once with ethyl acetate and dried under reduced pressure (5 mmHg) at 90° C. for three hours, to thereby yield 0.595 g of white crystals (first crystals) (49%). The filtrate from which the first crystals had been separated was concentrated under reduced pressure, and the residue was co-boiled once with ethanol (6 mL). The residue was dissolved in ethanol (6 mL) with heating. The solution was allowed to stand at 25° C. for two days. Similar to recovery of the first crystals, second crystals were recovered through filtration, followed by drying, to thereby yield 0.211 g of white crystals (second crystals) (17%).

Through powder X-ray diffractometry, the thus-yielded crystals (first crystals) exhibited characteristic peaks at the diffraction angles (2θ) of 4.60, 9.10, 13.02, 14.58, 16.68, 17.92, 19.14, 20.78, 21.36, and 24.76 (see FIG. 3).

Example 3

Production of Crystalline 5'-O-(4-monomethoxytrityl)pseudouridine

Pseudouridine (0.61 g, 2.5 mmol) was dehydrated through co-boiling twice with pyridine (5 mL) which had been dried with Molecular Sieves 4 A and suspended in pyridine (9.8 mL).

Under stirring at room temperature, 4-methoxytrityl chloride (0.926 g, 3 mmol) was added to the suspension. The mixture was placed in a vessel closed with a ground glass stopper and stirred at room temperature for 15 hours.

Water (1 mL) was added to the reaction mixture at room temperature, and the mixture was concentrated under reduced pressure. Ethyl acetate (15 mL) was added to the residue, and the mixture was washed twice with water (4 mL) and once with aqueous saturated sodium bicarbonate (4 mL). The organic layer was dried over sodium sulfate anhydrate, followed by concentration under reduced pressure. The residue was co-boiled once with ethyl acetate (7.7 mL). The residue was dissolved in ethyl acetate (15 mL) with heating. The solution was allowed to stand at 25° C. for two hours, and the precipitated crystals were recovered through filtration by means of a glass filter.

The crystals recovered through filtration were washed once with ethyl acetate, and co-boiled once with ethanol (10.4 mL). The residue was dissolved in ethanol (10.4 mL) with heating, and the solution was allowed to stand at 25° C. for 18 hours. The precipitated crystals were recovered through filtration by means of a funnel (product of Kiriyama Glass Co.).

The crystals were washed once with ethyl acetate and dried under reduced pressure (5 mmHg) at 90° C. for three hours, to thereby yield 0.582 g of white crystals (first crystals) (45%). The filtrate from which the first crystals had been separated was concentrated under reduced pressure, and the residue was co-boiled once with ethanol (5 mL). The residue was dissolved in ethanol (5 mL) with heating. The solution was allowed to stand at 25° C. for one day. Similar to recovery of the first crystals, second crystals were recovered through filtration, followed by drying, to thereby yield 0.169 g of white crystals (second crystals) (13%).

Through powder X-ray diffractometry, the thus-yielded crystals (first crystals) exhibited characteristic peaks at the diffraction angles (2θ) of 4.60, 9.76, 12.20, 12.94, 16.60, 17.84, 18.52, 19.04, 20.66, 21.24, 21.70, and 24.60 (see FIG. 4).

Test Example 1

Purity

The purity of the crystalline 5'-O-(4,4'-dimethoxytrityl)pseudouridine produced in Example 1 was determined through high-performance liquid chromatography (HPLC). Table 1 shows the results. HPLC was performed under the following conditions.

Column: YMC-Pack ODS-A A-312 (6.0×150 mm, 5 μm)
Mobile phase: 70% $CH_3CN$-50 mM TEAA
Flow rate: 0.5 mL/min
UV: 260 nm
Temperature: room temperature

TABLE 1

|  | Percent area (%) | | |
| --- | --- | --- | --- |
|  | Crystals of the invention | Analogous compound 1 | Analogous compound 2 |
| 1st crystals | 99.4 | 0.2 | 0.1 |
| 2nd crystals | 98.9 | 0.5 | 0.3 |

Analogous compounds 1 and 2: Unidentified, but conceivably 2',5'-O-di(4,4'-dimethoxytrityl)pseudouridine or 3',5'-O-di(4,4'-dimethoxytrityl)pseudouridine.

Test Example 2

Water Content

The water content of the crystalline 5'-O-(4,4'-dimethoxytrityl)pseudouridine produced in Example 1 was determined through the Karl Fischer's method (coulemetric titration, vaporization temperature: 130° C.). Although water content varies in response to the dryness of the sample, the crystalline 5'-O-(4,4'-dimethoxytrityl)pseudouridine produced in Example 1 was found to have a water content (w/w) of 1.3% (first crystals) and 1.7% (second crystals).

Test Example 3

Stability (1)

The crystalline 5'-O-(4,4'-dimethoxytrityl)pseudouridine produced in Example 1 was maintained in a sealed vessel at 60° C. and a relative humidity of 30%. Thereafter, the percent remaining of the compound was determined through HPLC, and the value was compared with that of the same compound in amorphous form, which had been separately prepared, so as to evaluate stability. Table 2 shows the results. The compound of crystal form was found to exhibit higher thermal stability than the compound of amorphous form.

TABLE 2

|  | Percent remaining (%) | | |
| --- | --- | --- | --- |
|  | Day 3 | Day 14 | Day 23 |
| Crystalline | 99.0 | 97.6 | 95.7 |
| Amorphous | 97.8 | 88.6 | 62.1 |

Test Example 4

Stability (2)

The crystalline 5'-O-(4,4'-dimethoxytrityl)pseudouridine produced in Example 1 was maintained in a desiccator at 25±2° C. and a relative humidity of 33%, 57%, or 75%. Fourteen days after, the percent remaining of the compound was determined through HPLC, and the value was compared with that of the same compound in amorphous form, which had been separately prepared, so as to evaluate stability. Table 3 shows the results. At a relative humidity of 75%, the stability clearly varied between the two samples. The compound in crystal form was found to be more stable against moisture.

TABLE 3

|  | Percent remaining (%) | | |
| --- | --- | --- | --- |
|  | RH 33% | RH 57% | RH 75% |
| Crystalline | 98.7 | 98.5 | 60.7 |
| Amorphous | 98.0 | 96.7 | 0.1 |

INDUSTRIAL APPLICABILITY

The present invention has first provided a stable and high-purity protected pseudouridine of crystal form. The method of the present invention, which does not need a silica gel column treatment, can be performed in a simple manner, does not impose a load on the environment, and realizes low-cost production of a target crystalline protected pseudouridine.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A crystalline 5' protected pseudouridine represented by the following structural formula:

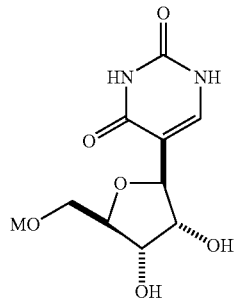

[F1]

wherein M is a dimethoxytrityl group, a monomethoxytrityl group, or a trityl group.

2. A crystalline 5' protected pseudouridine as described in claim 1, wherein M is a 4,4'-dimethoxytrityl group.

3. A crystalline 5' protected pseudouridine as described in claim 1, which has a purity of 98% (w/w) or higher.

4. A method for producing a crystalline 5' protected pseudouridine comprising crystallizing a protected pseudouridine from a solution containing the protected pseudouridine, by use of an ester solvent and an alcoholic solvent; and forming the crystalline protected pseudourine having the formula:

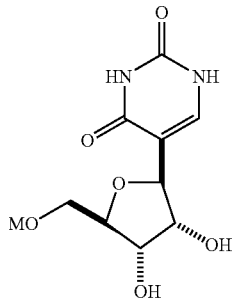

wherein M is a dimethoxytrityl group, a monomethoxytrityl group, or a trityl group.

5. A method described in claim 4, wherein the ester solvent is an acetic acid ester selected from the group consisting of ethyl acetate, methyl acetate, and n-butyl acetate.

6. A method described in claim 5, wherein the alcoholic solvent is a linear or branched alcohol having seven or less carbons selected from the group consisting of ethanol, methanol, and isopropanol.

7. A method described in claim 5, wherein the ester solvent is ethyl acetate, and the alcoholic solvent is ethanol.

8. A method described in claim 5, wherein crude crystals are produced from the ester solvent, and the crude crystals are recrystallized from an alcoholic solvent.

* * * * *